(12) United States Patent  (10) Patent No.: US 8,241,345 B2
Phung  (45) Date of Patent: Aug. 14, 2012

(54) STENT DELIVERY SYSTEM (75) Inventor: Mark Phung, Union City, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 164 days.

(21) Appl. No.: 12/847,241

(22) Filed: Jul. 30, 2010

(65) Prior Publication Data

US 2011/0190862 A1    Aug. 4, 2011

Related U.S. Application Data

(60) Provisional application No. 61/230,048, filed on Jul. 30, 2009.

(51) Int. Cl.
*A61F 2/84* (2006.01)
(52) U.S. Cl. ........................ 623/1.11; 623/1.12; 606/108
(58) Field of Classification Search ................. 623/1.11, 623/1.12; 606/108
See application file for complete search history.

(56) References Cited

U.S. PATENT DOCUMENTS

| 5,824,041 | A | 10/1998 | Lenker et al. |
| 2002/0183827 | A1 | 12/2002 | Derus et al. |
| 2004/0204749 | A1 | 10/2004 | Gunderson |
| 2006/0100531 | A1* | 5/2006 | Moser .......................... 600/486 |
| 2007/0118207 | A1* | 5/2007 | Amplatz et al. ............. 623/1.12 |
| 2008/0221703 | A1* | 9/2008 | Que et al. ................... 623/23.65 |

OTHER PUBLICATIONS

PCT Invitation to Pay Additional Fees from the International Search Authority for PCT/US2010/043984, Applicant Boston Scientific Scimed, Inc., Form PCT/ISA/206 and Annex to Form PCT/ISA/206, dated Oct. 28, 2010 (7 pages).
PCT International Search Report and Written Opinion for PCT/US2010/043984, Applicant Boston Scientific Scimed, Inc., Forms PCT/ISA/210, 220, and 237, dated Jan. 14, 2011 (17 pages).

* cited by examiner

*Primary Examiner* — William H. Matthews
*Assistant Examiner* — Randy Shay
(74) *Attorney, Agent, or Firm* — Vista IP Law Group LLP (57) ABSTRACT

A stent delivery system comprises a stent having a first connector disposed on a stent proximal end, and a pusher wire having a second connector disposed on a pusher wire distal end, wherein the first and second connectors are configured to releasably attach to each other.

2 Claims, 7 Drawing Sheets

STENT DELIVERY SYSTEM

RELATED APPLICATION DATA

The present application claims the benefit under 35 U.S.C. §119 to U.S. provisional patent application Ser. No. 61/230,048, filed Jul. 30, 2009. The foregoing application is hereby incorporated by reference into the present application in its entirety.

FIELD OF THE INVENTION

The field of the invention generally relates to devices for delivering stents into body lumens.

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent may be biased so as to expand upon release from the delivery catheter and/or include a shape-memory component which allows the stent to expand upon exposure to a predetermined condition. Some stents may be characterized as hybrid stents which have some characteristics of both self-expandable and balloon expandable stents.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or sheet of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern. The density of the braid in braided stents is measured in picks per inch. Stents may include components that are welded, bonded or otherwise engaged to one another.

A self-expanding stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel to be treated is exposed by minor surgical means. In such techniques, a microcatheter is threaded through the vascular system until its distal end reaches the implantation site. Then a compressed stent is introduced into the proximal end of the microcatheter and pushed through the microcatheter to its distal end using a pusher wire. When the stent is positioned at the correct location, it is pushed out of the microcatheter (i.e., unsheathed) and caused or allowed to expand to a predetermined diameter in the vessel.

Perceived problems with current stent delivery systems include inability to re-sheath stents that have been partially unsheathed, about 50-80%. Perceived problems also include lack of stability at the junction between the distal end of the pusher wire and the proximal end of the stent. Another perceived problem is that individual braid wires at both the proximal and distal ends of braided stents tend to flare out into the microcatheter wall as the stent is pushed through the microcatheter. Further, perceived problems include radial expansion of the stent during delivery as the stent is pushed through a microcatheter. The last two perceived problems increase frictional resistance as a stent is pushed through a microcatheter.

SUMMARY

In one embodiment, a stent delivery system comprises a stent having a first connector disposed on a stent proximal end; and a pusher wire having a second connector disposed on a pusher wire distal end, wherein the first and second connectors are configured to releasably attach to each other. The delivery system may further comprise a catheter, wherein the pusher wire is coaxially disposed within a lumen of the catheter.

In some embodiments, the first and second connectors are configured to transmit sufficient force to re-sheath a partially unsheathed stent without detaching from each other.

In some embodiments, the first connector is a loop, the second connector comprising a protrusion, wherein the loop is proximal of the protrusion, so that when the pusher wire is pulled proximally relative to the stent, the loop pulls the protrusion, which in turn pulls the stent proximally.

In some embodiments, the first connector may be a bent wire, the second connector comprising a cavity that defines a shape that approximates a shape of the bent wire, wherein the bent wire is biased radially inward, so that the bent wire is biased into the cavity and when the pusher wire is pulled proximally, a wall of the cavity pulls the bent wire, which in turn pulls the stent proximally.

In some embodiments, the first connector comprises a flattened element and the second connector comprises a cavity that defines a shape that approximates a shape of the flattened element, wherein the flattened element is biased radially inward, so that the flattened element is biased into the cavity and when the pusher wire is pulled proximally, a wall of the cavity pulls the flattened element, which in turn pulls the stent proximally.

In some embodiments, the pusher wire may include a proximal bumper disposed on the pusher wire; a re-sheathing bumper disposed on the pusher wire distal of the proximal bumper; a middle bumper disposed on the pusher wire distal of the re-sheathing bumper; and a distal bumper disposed on the pusher wire distal of the middle bumper. In such embodiments, the stent may be disposed on the pusher wire between the proximal and distal bumpers, wherein the first connector comprises a detent and the second connector comprises a notch defined by the respective proximal and re-sheathing bumpers. In some such embodiments, the detent is disposed in the notch, so that when the pusher wire is pulled proximally, the re-sheathing bumper pulls the detent, which in turn pulls the stent proximally.

BRIEF DESCRIPTION OF THE DRAWINGS

Referring now to the drawings in which like reference numbers represent corresponding parts throughout, and in which.

DETAILED DESCRIPTION OF THE ILLUSTRATED EMBODIMENTS

Figure 1:
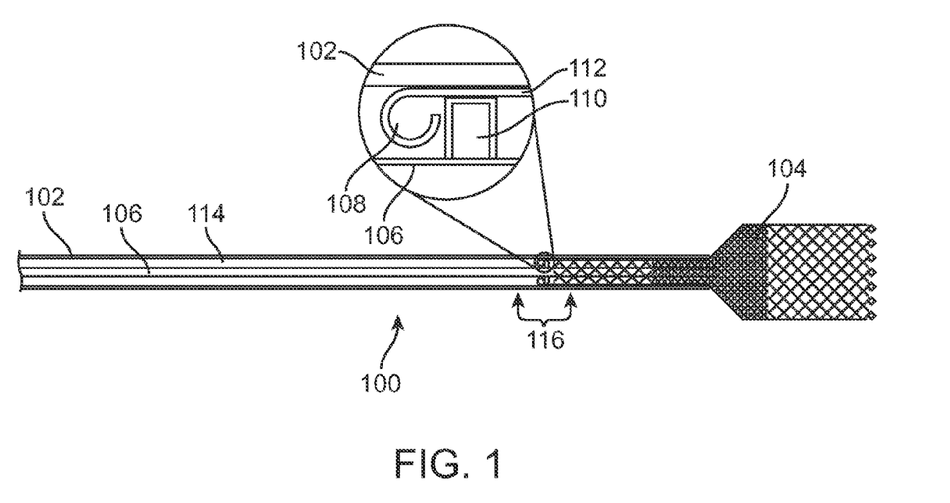
FIG. 1 is a longitudinal cross sectional view of a stent delivery system in accordance with one embodiment of the invention, wherein a portion of the system is magnified in an inset.

FIG. 1 illustrates a stent delivery system 100 according to an embodiment of the invention. The stent delivery system 100 has a catheter 102, a stent 104, and a pusher wire 106. As seen in the FIG. 1 inset, the proximal end of the stent 104 ends in a loop 108 and the pusher wire 106 includes a lateral protrusion 110 disposed near the loop 108. The loop 108 and the protrusion 110 are two connectors that releasably attach the stent 104 and the pusher wire 106. The pusher wire 106 may extend into the stent 104, as shown in FIG. 1, or the pusher wire 106 may end at the proximal end of the stent 104.

The stent 104 can be made from metallic and non-metallic materials. Metallic materials include, without limitation, nitinol, stainless steel, cobalt-based alloy such as Elgiloy, platinum, gold, titanium, tantalum, niobium, and combinations thereof and other biocompatible materials, as well as polymeric materials. Metallic stent materials may have an inner core of tantalum, gold, platinum, iridium or combinations of thereof and an outer member or layer of nitinol to provide a composite filament for improved radiopacity or visibility. Non-metallic materials include, without limitation, polyesters, such as polyethylene terephthalate (PET) polyesters, polypropylenes, polyethylenes, polyurethanes, polyolefins, polyvinyls, polymethylacetates, polyamides, naphthalane dicarboxylene derivatives, natural silk, and polytetrafluoroethylenes. Non-metallic materials also include carbon, glass, and ceramics. Stents 104 made from memory material, e.g. nitinol, could be biased to take on an expanded form due to the memory property of the filament material. In braided stents, the loop 108 can be formed by heat treating an extended braid filament 112 on the proximal end of the stent 104. Alternatively, the loop 108 may be preformed and bonded to the stent 104.

The catheter 102 can be made from any suitable bio-compatible material and lined with a low friction material like Teflon™. The pusher wire 106 can be made from a hypotube or a solid wire. The protrusion 110 can be preformed and bonded to the pusher wire 106. An alternative embodiment includes a second catheter (not shown) that forms a sheath between the catheter 102 and the stent 104 and pusher wire 106.

The FIG. 1 inset shows that the loop 108 is proximal to, i.e. to the left of in the figures in this application, the protrusion 110. Because of the tight fit in the lumen 114 of the catheter 102, the protrusion 110 abuts the loop 108 proximally. When the pusher wire 106 is pulled proximally, the protrusion 110 pulls the loop 108 proximally, which in turn pulls the stent 104 proximally. The protrusion 110 also abuts the inside of the stent 104 radially due to the tight fit in the lumen 114 of the catheter 102. When the pusher wire 106 is pushed distally, the lateral protrusion 110 pushes the stent 104 distally through the catheter 102 like the bumpers describe herein.

The junction 116 created by the catheter 102, the loop 108, and the protrusion 110 is sufficiently strong to pull a partially unsheathed stent 104 back into the catheter 102 from which the stent 104 was deployed. For instance, FIG. 1 shows a stent 104 that is about 50% deployed. Pulling the pusher wire 106 proximally will pull the stent 104 back into the catheter 102 and radially collapse the stent 104.

Figure 2:
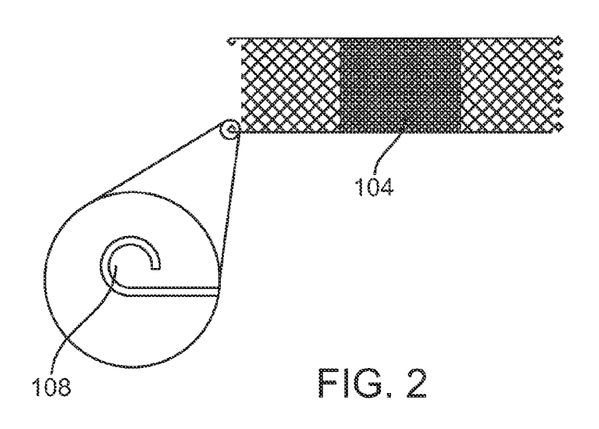
FIG. 2 is a longitudinal cross sectional view of a stent in accordance with one embodiment of the invention, wherein a portion of the stent is magnified in an inset.

Once the self-expanding stent 104 is pushed out of the catheter 102, it becomes fully expanded, as shown in FIG. 2. Once the stent 104 is expanded, the loop 108 no longer abuts the protrusion 110. Then the pusher wire 106 and the catheter 102 can be withdrawn proximally, leaving the stent 104 at its insertion point in the vascular system.

Figure 3:
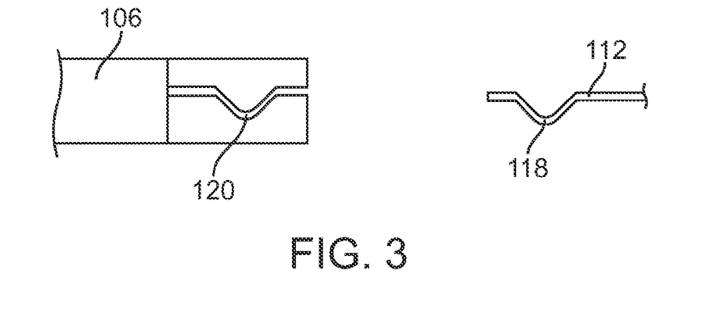
FIG. 3 is a detailed side view of two connectors in accordance with one embodiment of the invention.
Figure 4:
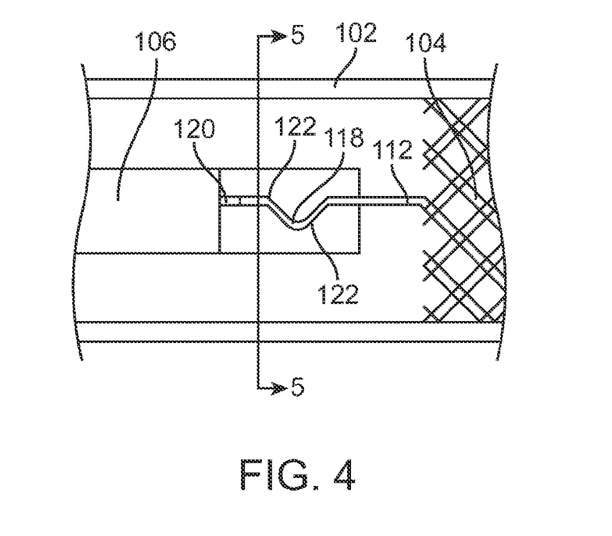
FIG. 4 is a detailed longitudinal cross sectional view of a stent/pusher wire junction in accordance with one embodiment of the invention.
Figure 5:
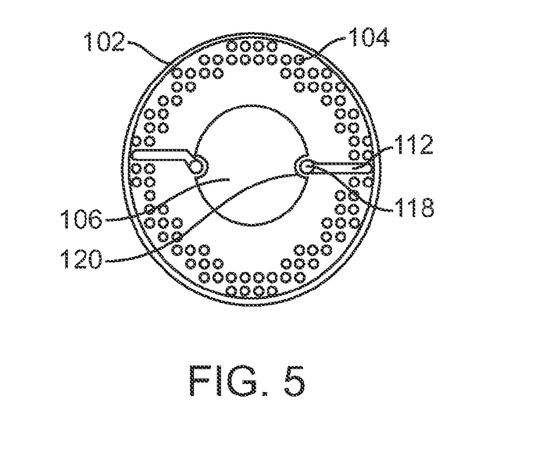
FIG. 5 is a detailed cross sectional view through the line 5-5 in FIG. 4.
Figure 6:
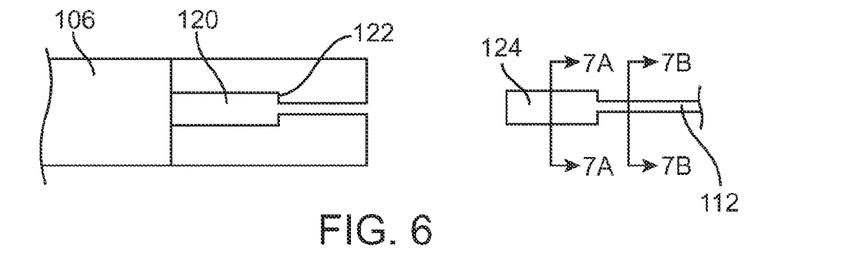
FIG. 6 is a detailed side view of two connectors in accordance with one embodiment of the invention.
Figure 7A:
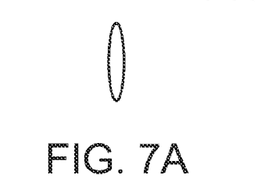
FIGS. 7A and 7B are detailed cross sectional view through the lines 7A-7A and 7B-7B in FIG. 6, respectively.
Figure 7B:
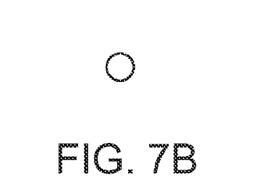

FIGS. 3-5 show a stent delivery system 100 according to another embodiment of the invention. In this embodiment, the connectors are a bent wire 118 connected to the stent 104, and a cavity 120 on the lateral surface of the pusher wire 106. The bent wire 118, which is shaped like a wave, can be formed by heat treating an extended braid filament 112 of the stent 104 as described above. Alternatively, the bent wire 118 can be preformed and bonded to the stent 104. The cavity 120 can be etched into the side of the hypotube that forms the pusher wire 106.

The extended braid filament 112 and the bent wire 118 are biased medially in a radial direction, as shown in FIG. 5. This bias pushes the bent wire 118 into the cavity 120 when the stent 104 is compressed around the pusher wire 106. The lumen 114 is a tight fit for the compressed stent 104 and the pusher wire 106. Therefore, when the bent wire 118 is urged into the cavity 120, as shown in FIGS. 4 and 5, the stent 104 and the pusher wire 106 are releasably attached and move as one body along the longitudinal axis of the catheter 102. Specifically, when the pusher wire 106 is pulled proximally, the distal surfaces 122 of the cavity 120 abut the bent wire 118 and pull the bent wire 118 and the stent 104 attached thereto in a proximal direction. Once the stent 104 completely exits the catheter 102, the stent 104 is expanded and the bent wire 118 exits the cavity 120, separating the deployed stent 104 from the pusher wire 106.

FIGS. 6-9 show a stent delivery system 100 according to yet another embodiment of the invention. In this embodiment, the connectors are a flattened element 124, and a cavity 120 on the lateral surface of the pusher wire 106. The flattened element 124, which has an ovoid cross section, as shown in FIG. 7A, can be formed by flattening an extended braid filament 112 of the stent 104. Alternatively, the flattened element 124 can be preformed and bonded to the stent 104. The cavity 120 can be etched into the side of the hypotube that forms the pusher wire 106.

Figure 8:
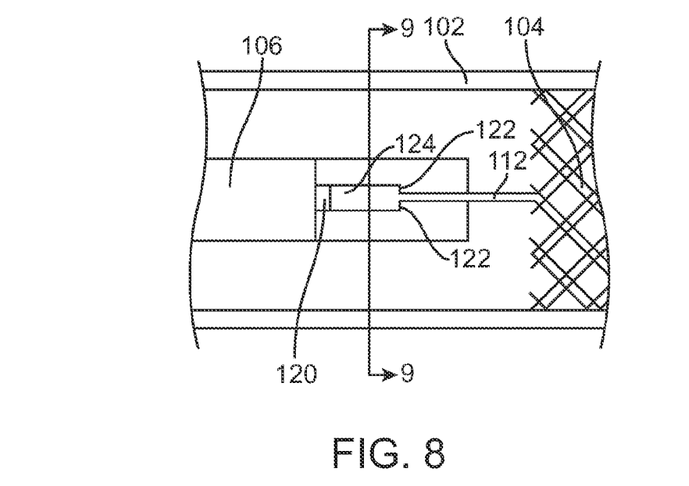
FIG. 8 is a detailed longitudinal cross sectional view of a stent/pusher wire junction in accordance with one embodiment of the invention.
Figure 9:
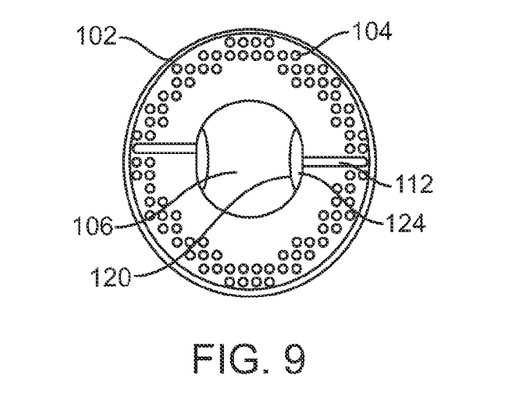
FIG. 9 is a detailed cross sectional view through the line 9-9 in FIG. 8.

The extended braid filament 112 and the flattened element 124 are biased medially in a radial direction, as shown in FIG. 9. This bias pushes the flattened element 124 into the cavity 120 when the stent 104 is compressed around the pusher wire 106. The lumen 114 is a tight fit for the compressed stent 104 and the pusher wire 106. Therefore, when the flattened element 124 is urged into the cavity 120, as shown in FIGS. 8 and 9, the stent 104 and the pusher wire 106 are releasably attached and move as one body along the longitudinal axis of the catheter 102. Specifically, when the pusher wire 106 is pulled proximally, the distal surfaces 122 of the cavity 120 abut the flattened element 124 and pull the flattened element 124 and the stent 104 attached thereto in a proximal direction. Once the stent 104 completely exits the catheter 102, the stent 104 is expanded and the flattened element 124 exits the cavity 120, separating the deployed stent 104 from the pusher wire 106.

FIGS. 10-13 show a stent delivery system 100 according to yet another embodiment of the invention. In this embodiment, the connectors are a plurality of detents 126, and a circular notch 128 formed by bumpers extending from the lateral surface of the pusher wire 106. The detents 126 can be formed by clipping platinum coupons or other markers to the ends of extended braid filaments 112 of the stent 104. Alternatively, the detents 126 can be preformed by shaping the ends of extended braid filaments 112. The bumpers are tube shaped radial protrusions made from soft deformable plastic such as polyurethanes or silicone, and bonded to the side of the hypotube that forms the pusher wire 106. Some bumpers (proximal and re-sheathing) that push or pull the stent may be made of metallic materials in form of coils, rings or short tubes and attached to the pusher wire 106.

Figure 10:
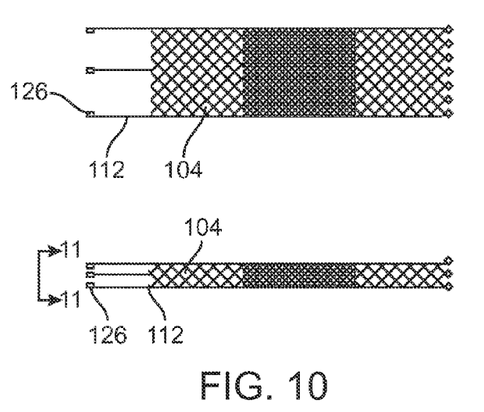
FIG. 10 shows two longitudinal cross sectional views of a stent in accordance with one embodiment of the invention.
Figure 12:
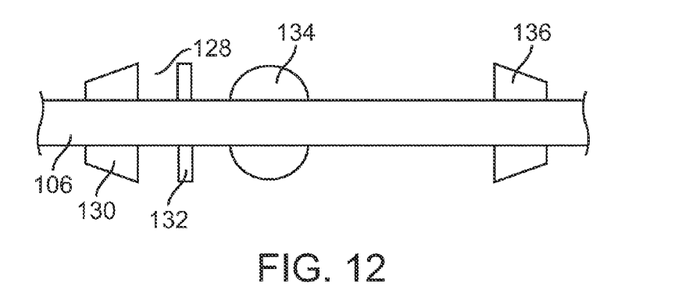
FIG. 12 is a detailed longitudinal cross sectional view of a pusher wire in accordance with one embodiment of the invention.
Figure 13:
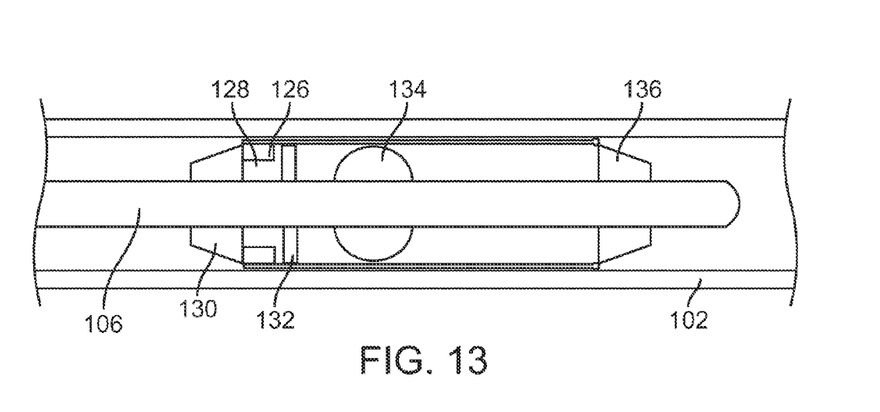
FIG. 13 is a detailed longitudinal cross sectional view of a stent/pusher wire junction in accordance with one embodiment of the invention.

This embodiment has four bumpers: a proximal bumper 130, a re-sheathing bumper 132, a middle bumper 134, and a distal bumper 136. Other embodiments have a plurality of middle bumpers 134. When the stent 104 is loaded onto the pusher wire 106, the proximal bumper 130 is proximal of the detents 126, and the re-sheathing bumper 132 is distal of the detents 126. The proximal bumper 130 and the re-sheathing bumper 132 form the notch 128 which houses the detents 126 when the stent 104 is loaded onto the pusher wire 106. The middle bumper 134 is in contact with the middle of the stent 104 and the distal bumper 136 is distal of the stent 104. When the stent 104 is loaded onto the pusher wire 106, all of the bumpers 130, 132, 134, 136 come into contact with the stent 104 or the detents 126. This increased contact provides greater control over the stent 104 during insertion and deployment.

Figure 11:
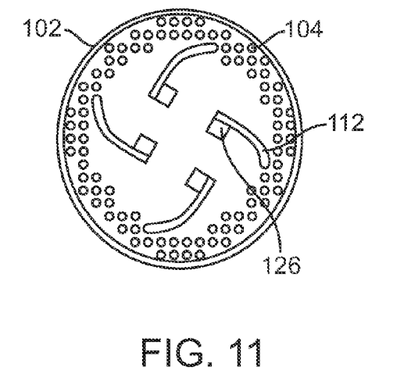
FIG. 11 is a detailed cross sectional view through the line 11-11 in FIG. 10.

The extended braid filament 112 and the detents 126 are biased medially in a radial direction, as shown in FIG. 11. This bias pushes the detents 126 into the notch 128 when the stent 104 is compressed around the pusher wire 106. The lumen 114 is a tight fit for the compressed stent 104 and the pusher wire 106. Therefore, when the detents 126 are urged into the notch 128, as shown in FIG. 13, the stent 104 and the pusher wire 106 are releasably attached and move as one body along the longitudinal axis of the catheter 102. Specifically, when the pusher wire 106 is pulled proximally, the re-sheathing bumper 132 abut the detents 126 and pull the detents 126 and the stent 104 attached thereto in a proximal direction. Once the stent 104 completely exits the catheter 102, the stent 104 is expanded and the detents 126 exit the notch 128, separating the deployed stent 104 from the pusher wire 106.

Figure 14:
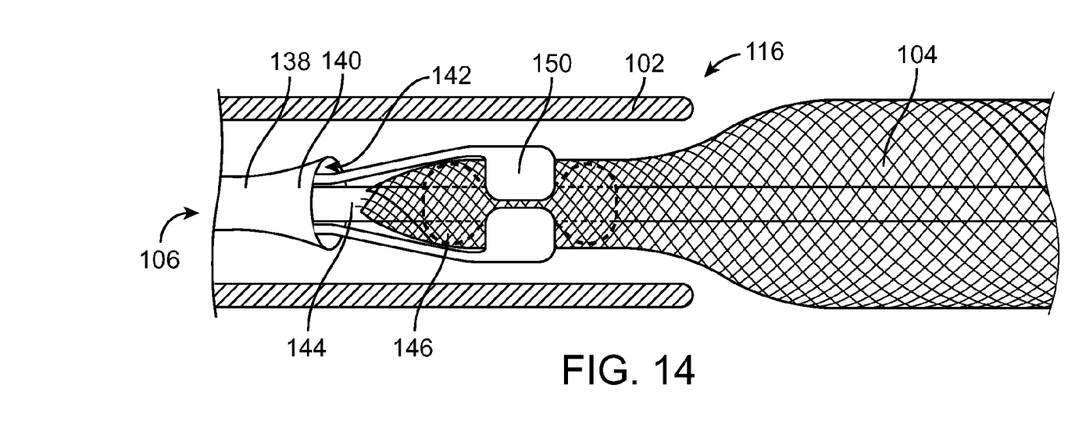
FIGS. 14 and 15 are detailed side perspective views of a stent/pusher wire junction in accordance with one embodiment of the invention, wherein the catheter has been cut away for clarity.
Figure 15:
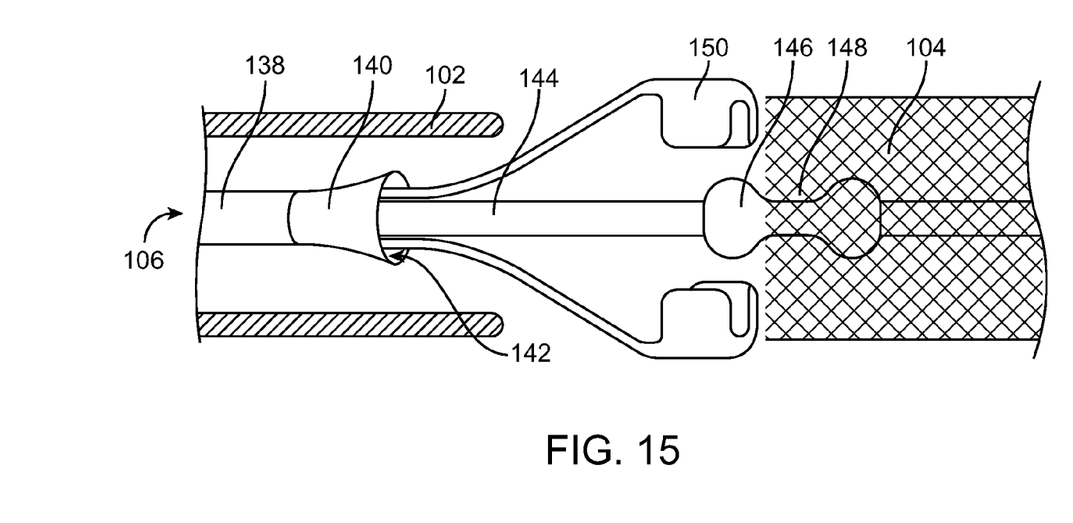

FIGS. 14 and 15 show a stent delivery system 100 according to still another embodiment of the invention. In this embodiment, the pusher wire 106 includes a hypotube 138 having a funnel shaped bumper 140 disposed on its distal end and defining a pusher wire lumen 142. The pusher wire 106 also includes a core wire 144 disposed in the pusher wire lumen 142 and having a middle bumper 146 disposed thereon. The middle bumper 146 is shaped like a goblet on its side, with depression 148 in the middle of the middle bumper 146. The pusher wire 106 also includes a pair of forceps-like holders 150 extending in a distal direction from the pusher wire lumen 142. The holders 150 are made from a shape memory material, like nitinol, and are biased in the open position, unless the holders 150 are restrained when inserted into a catheter 102 or the holders 150 are urged to close by being pulled proximally into the funnel shaped bumper 140.

When the holders 150 are closed, they close around the depression 148 in the middle bumper 146. A stent 104 is loaded onto the pusher wire 106 by threading the proximal end of the stent 104 between the holders 150 and the middle bumper 146. Then the holders 150 and the core wire 144 are pulled proximally into the pusher wire lumen 142 until the holders 150 close around the depression 148 and hold the stent 104 to the middle bumper 146. Because the pusher wire lumen 142 is smaller than the cross sectional area of the holders 150 closed around the middle bumper 146, neither the holders 150 nor the middle bumper 146 can be pulled proximally into the pusher wire lumen 142. When the holders 150 are closed around the stent 104 and the middle bumper 146, the stent 104 and the pusher wire 106 are releasably attached and move as one body along the longitudinal axis of the catheter 102. Specifically, when the pusher wire 106 is pulled proximally, the holders 150 and the middle bumper 146 pull the stent 104 in a proximal direction. Once the stent 104 completely exits the catheter 102, the holders 150 expand and the deployed stent 104 is separated from the pusher wire 106, as in FIG. 15.

In an alternative embodiment, there is no relative motion between the core wire 144 and the pusher wire lumen 142. In fact, the pusher wire 106 can be a solid wire without a pusher wire lumen 142 or a core wire 144. In this embodiment, deformation of the holders 150 inside of the microcatheter 102 closes the holders 150 around the depression 148, and holds the stent 104 onto the middle bumper 146. Once the holders 150 exit the microcatheter 102, the holders 150 release to deploy the stent 104.

Figure 16:
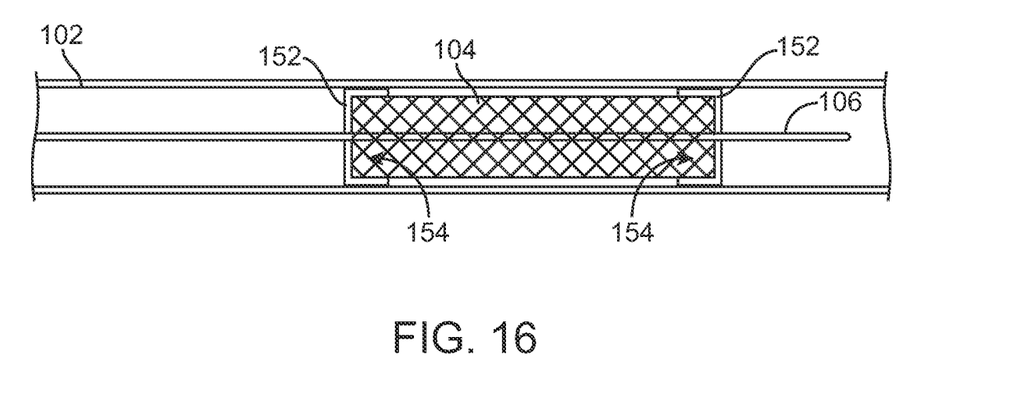
FIGS. 16-19 are longitudinal cross sectional views of stent/pusher wire junctions in accordance with various embodiments of the invention.
Figure 17:
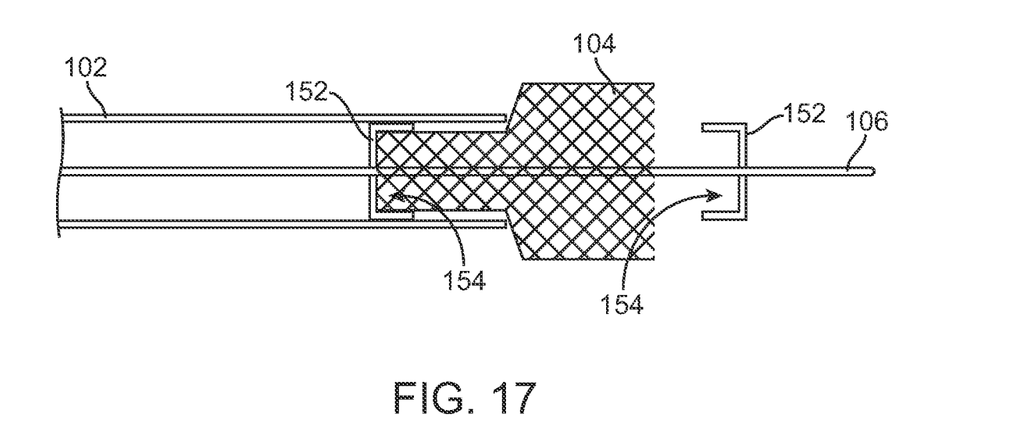

FIGS. 16 and 17 show another embodiment of the invention in which the stent 104 is held onto the pusher wire 106 with one or two cups 152 that are fixed to the pusher wire 106. When two cups are used, the cups 152 are configured so that their openings 154 face each other. The cups 152 are preformed, and then bonded to the pusher wire 106. A compressed stent 104 is loaded over the pusher wire 106 with each end of the stent 104 held in a cup 152. As long as the stent 104 is in the catheter 102, it is prevented from expanding and stays in its compressed shape. In this form, the cups 152 translate any force applied to the pusher wire 106 to the stent 104 and allow it to be moved along the longitudinal axis of the catheter 102. When the stent 104 exits the catheter 102, the stent 104 expands radially and shortens along the longitudinal axis, as shown in FIG. 17. When both ends of the stent 104 have expanded and shortened out of their respective cups 152, the catheter 102 and the pusher wire 106 can be removed proximally.

Figure 18:
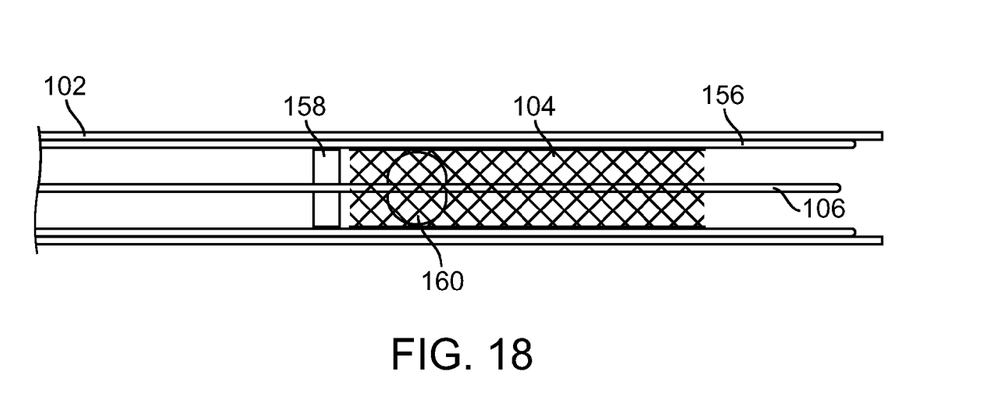
Figure 19:
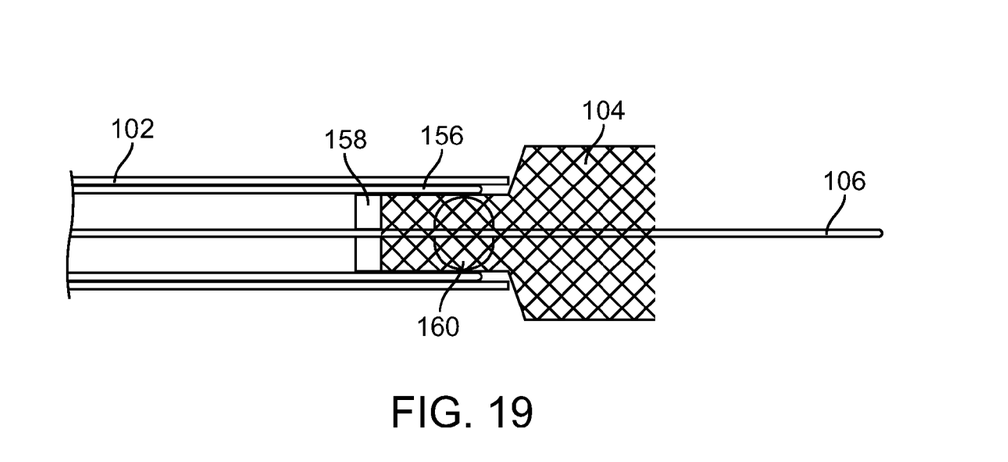

FIGS. 18 and 19 show yet another embodiment of the invention in which the stent 104 is completely contained by a sheath 156. A proximal bumper 158 and a middle bumper 160 attached to the pusher wire 106 allow the stent 104 to be held in place while the sheath 156 and the catheter 102 are retracted proximally to expose the stent 104, as in FIG. 19. The stent is pushed outside of the catheter 102 before withdrawing the sheath 156 while holding the pusher wire 106 stationary. As long as the sheath 156 still overlaps the middle bumper 160, the stent 104 can be pulled back into the catheter 102 because it has not been released. Once the sheath 156 is fully retracted proximal to the proximal bumper 158, the stent 104 will not be re-sheathable. If the sheath 156 and the catheter 102 are both retracted proximal to proximal bumper 158, the stent 104 will expand radially to its deployed size. The proximal bumper 158 is preformed, and then bonded to the pusher wire 106. The middle bumper 160 is a tube shaped radial protrusion made from soft deformable plastic such as polyurethanes or silicone, and bonded to the side of the hypotube that forms the pusher wire 106.

While various embodiments of the present invention have been shown and described, they are presented for purposes of illustration, and not limitation. Various modifications may be made to the illustrated and described embodiments without departing from the scope of the present invention, which is to be limited and defined only by the following claims and their equivalents.

What is claimed is:

1. A stent delivery system, comprising:
    a pusher wire, comprising:
        a tubular body having a pusher wire lumen;
        an elongate body disposed in the pusher wire lumen;
        a funnel shaped bumper disposed on a distal end of the tubular body;
        a pair of holders disposed on the elongate body;
        a middle bumper disposed on the elongate body distal of the pair of holders, wherein the pair of holders is configured to close around the middle bumper and secure a stent thereto when the elongate body is pulled proximally into the tubular body; and
    a catheter having a proximal end, a distal end, and a catheter lumen extending between the proximal end and the distal end,
    wherein the pusher wire is coaxially disposed within a lumen of the catheter, and
    wherein an opening of the funnel shaped bumper is smaller than a cross sectional area of the pair of holders when closed around the middle bumper.

2. The system of claim 1, wherein the pair of holders is biased in an open position.

\* \* \* \* \*